US010466238B2

(12) United States Patent
Sousa Martin et al.

(10) Patent No.: US 10,466,238 B2
(45) Date of Patent: *Nov. 5, 2019

(54) DETERMINATION OF LEVELS OF IMMUNOGENIC GLUTEN PEPTIDES IN HUMAN SAMPLES

(71) Applicant: UNIVERSIDAD DE SEVILLA, Seville (ES)

(72) Inventors: Carolina Sousa Martin, Seville (ES); Isabel Comino Montilla, Seville (ES); Ana Real Calderon, Seville (ES); Santiago Vivas Alegre, Seville (ES); Angel Cebolla Ramirez, Seville (ES)

(73) Assignee: UNIVERSIDAD DE SEVILLA, Seville (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,906

(22) Filed: Jul. 5, 2016

(65) Prior Publication Data

US 2016/0320385 A1    Nov. 3, 2016

Related U.S. Application Data

(63) Continuation-in-part of application No. 13/977,247, filed as application No. PCT/ES2011/000379 on Dec. 28, 2011, now Pat. No. 9,410,962.

(30) Foreign Application Priority Data

Dec. 28, 2010   (ES) .................................. 201001633

(51) Int. Cl.
*G01N 33/53*   (2006.01)
*G01N 33/564*   (2006.01)

(52) U.S. Cl.
CPC ..... *G01N 33/564* (2013.01); *G01N 2333/415* (2013.01); *G01N 2800/06* (2013.01); *G01N 2800/52* (2013.01)

(58) Field of Classification Search
CPC ............. G01N 33/564; G01N 2800/52; G01N 2333/415; G01N 2800/06
See application file for complete search history.

(56) References Cited

U.S. PATENT DOCUMENTS

| 4,208,479 | A | 6/1980 | Zuk et al. |
| 7,563,864 | B2 | 7/2009 | Marti et al. |
| 2006/0189540 | A1 | 8/2006 | Khosla et al. |
| 2014/0178903 | A1* | 6/2014 | Sousa Martin .... G01N 33/5308 435/7.92 |

FOREIGN PATENT DOCUMENTS

| WO | WO2012089868 | * | 7/2012 | |
| WO | WO 2013098441 | * | 7/2014 | ............ G01N 33/02 |

OTHER PUBLICATIONS

WO 2013098441 Machine Translation; 2013.*
E. A. Padlan, Adv Prot Chem 49:57-133; 1996 (PTO-892).*
Corada et al., Blood, 2001; 97:1679-84.*
H. Wieser, "Chemistry of gluten proteins", Food Microbiology 24 (2007) pp. 115-119.
A. Fasano, "Surprises from Celiac Disease", Scientific American, Aug. 2009, pp. 32-39.
R.H. Erickson, "Digestion and Absorption of Dietary Protein", Annual Review of Medicine 1990, 41, pp. 133-139.
V. Ganapathy, "Protein Digestion and Absorption", Physiology of the Gastrointestinal Tract, Fourth Edition, Academic Press, 2006, pp. 1667-1692.
M.T. Bethune, "Parallels between Pathogens and Gluten Peptides in Celiac Sprue, PLoS Pathogens", Feb. 2008, vol. 4, Issue 2, e34, pp. 1-16, www.plospathogens.org.
B. Jabri, "Tissue-mediated control of immunopathology in coeliac disease", Nature, Dec. 2009, vol. 9, pp. 858-870, www.nature.com/reviews/immunol.
A. Alaedini, "Narrative Review: Celiac Disease: Understanding a Complex Autoimmune Disorder", Annals of Internal Medicine, Feb. 15, 2015, pp. 289-298.
A. Fasano, "Celiac Disease", New England Journal of Medicine, 367; 25, Dec. 20, 2012, pp. 2419-2426.
G.J. Tack, "The spectrum of celiac disease: epidemiology, clinical aspects and treatment", Nature Reviews, Gastroenterology & Hepatology, vol. 7, Apr. 2010, pp. 204-213.
L. Shan, "Structural Basis for Gluten Intolerance in Celiac Sprue", Science, vol. 297, Sep. 27, 2002, pp. 2275-2279.
M.T. Bethune, "Noninflammatory Gluten Peptide Analogs as Biomarkers for Celiac Sprue", Chem Biol. Aug. 28, 2009; 16(8): pp. 868-881. doi:10.1016/j. chembiol.2009.07.009.
J.A. Tye-Din, "Comprehensive, Quantitative Mapping of T Cell Epitopes in Gluten in Celiac Disease", Science Translational Medicine, vol. 2, Issue 41, 41ra51, Jul. 21, 2010, pp. 1-14.
C. Ciacci, "Long-Term Follow-Up of Celiac Adults on Gluten-Free Diet: Prevalence and Correlates of Intestinal Damage", Digestion, 2002; 66: pp. 178-185.

(Continued)

*Primary Examiner* — Julie Wu
*Assistant Examiner* — Carmencita M Belei
(74) *Attorney, Agent, or Firm* — Karl Bozicevic; Bozicevic, Field & Francis LLP

(57) ABSTRACT

The present invention fitted in the medical-clinical sector, shows a method for monitoring the ingestion of gluten by measuring protein/gluten peptides present in fecal samples with antibodies against immunogenic peptides resistant to gastrointestinal digestion. The presence or absence of these immunogenic peptides is controlled by immunological assays based on antibodies reactive against immunogenic gluten peptides that are resistant to proteolysis. These assays may be quantitative techniques ELISAs, or qualitative as rapid immunochromatographic assays, immunoblots, etc. These measures may also be applied to verify compliance with the gluten-free diet, to improve diagnosis in cases of refractory or severe symptoms of celiac disease in which a gluten-free diet is supposedly being respected, or to clinical research on the effectiveness of enzymatic therapies related with prolamin detoxification.

Figure 1A:
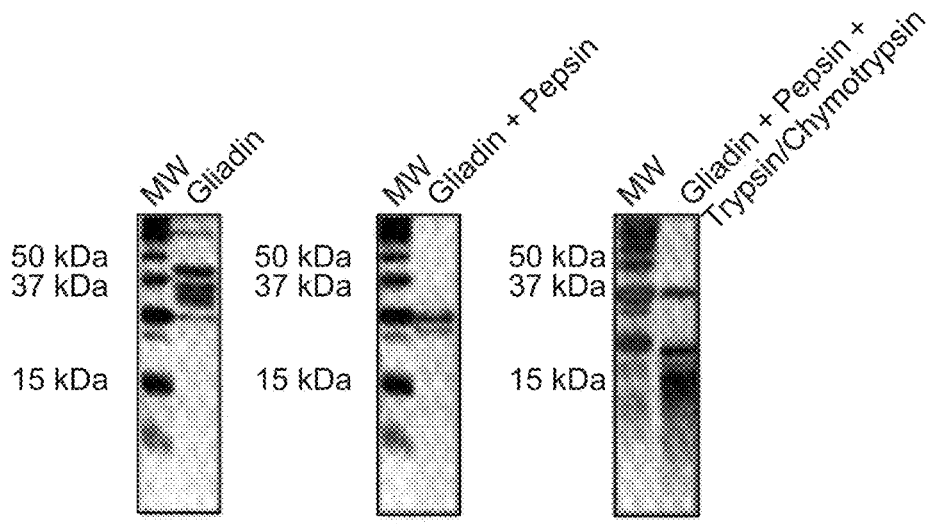

4 Claims, 8 Drawing Sheets
Specification includes a Sequence Listing.

(56) References Cited

OTHER PUBLICATIONS

J.A. Silvester, "Long-term follow-up of individuals with celiac disease: an evaluation of current practice guidelines", Canadian Journal of Gastroenterology & Hepatology, vol. 21, No. 9, Sep. 2007, pp. 557-564.
A. Al-Toma, "The Management of Complicated Celiac Disease", Digestive Diseases, 2007; 25: pp. 230-236.
H.J. Freeman, "Adult Celiac Disease and Its Malignant Complications", Gut and Liver, vol. 3, No. 4, Dec. 2009, pp. 237-246.
A. Rubio-Tapia, "Classification and Management of Refractory Celiac Disease", Gut. Apr. 2010; 59(4): pp. 547-557.
P. Fernandez-Calle, "Is an intestinal permeability test a valid marker for slight dietary transgressions in adolescents with coeliac disease?" Gut 1993; 34: pp. 774-777.
D.R. Duerksen, "Intestinal permeability in Long-Term Follow-up of Patients with Celiac Disease on a Gluten-Free Diet", Digestive Diseases and Sciences, vol. 50, No. 4, Apr. 2005, pp. 785-790.
M. Ayse Selimoglu, "Celiac Disease Prevention and Treatment", Journal of Clinical Gastroentrology, vol. 44, No. 1, Jan. 2010, pp. 4-8.
B. Moron, "Sensitive detection of cereal fractions that are toxic to celiac disease patients by using monoclonal antibodies to a main immunogenic wheat peptide", The American Journal of Clinical Nutrition, 2008; 87: pp. 405-414.
B. Moron, "Toward the Assessment of Food Toxicity for Celiac Patients: Characterization of Monoclonal Antibodies to a Main Immunogenic Gluten Peptide", PLos One, May 2008, vol. 3, Issue 5, e2294, pp. 1-13.
J. Ehren, "A Food-Grade Enzyme Preparation with Modest Gluten Detoxification Properties", PLoS One, Jul. 2009, vol. 4, Issue 7, e6313, pp. 1-10.
R. Van Eckert, "Towards a new gliadin reference material-isolation and characterisation", Journal of Cereal Science 43 (2006), pp. 331-341.
L. Shan, "Identification and Analysis of Multivalent Proteolytically Resistant Peptides from Gluten: Implications for Celiac Sprue", Journal of Proteome Research, 2005; 4(5); pp. 1732-1741.
C. Sousa, "Translational and Structural Requirements of the Early Nodulin Gene enod40, a Short-Open Reading Frame-Containing RNA, for Elicitation of a Cell-Specific Growth Response in the Alfalfa Root Cortex", Molecular and Cellular Biology, Jan. 2001, vol. 21, No. 1, pp. 354-366.
M. Stasse-Wolthuis, "The effect of a natural high-fiber diet on serum lipids, fecal lipids, and colonic function", The American Journal of Clinical Nutrition 32: Sep. 1979, pp. 1881-1888.
Millipore Application Guide, 2008, retrieved from USPTO from parent application Jul. 2016.
Catassi et al., "A Prospective, Double-Blind, Placebo-Controlled Trial to Establish a Safe Gluten Threshold for Patients With Celiac Disease 1-3", Am. J. Clin. Nutr., 2007, pp. 160-166.
Korponay-Szabo, "Population screening for coeliac disease in primary care by district nurses using a rapid antibody test: diagnostic accuracy and feasibility study", BMJ, Online First, pp. 1-9, bjm. com (2007).

\* cited by examiner

LQLQPFPQPQLPYPQPQLPYPQPQLPYPQPQPF    33-mer
SEQ ID NO: 1
FIG. 2A
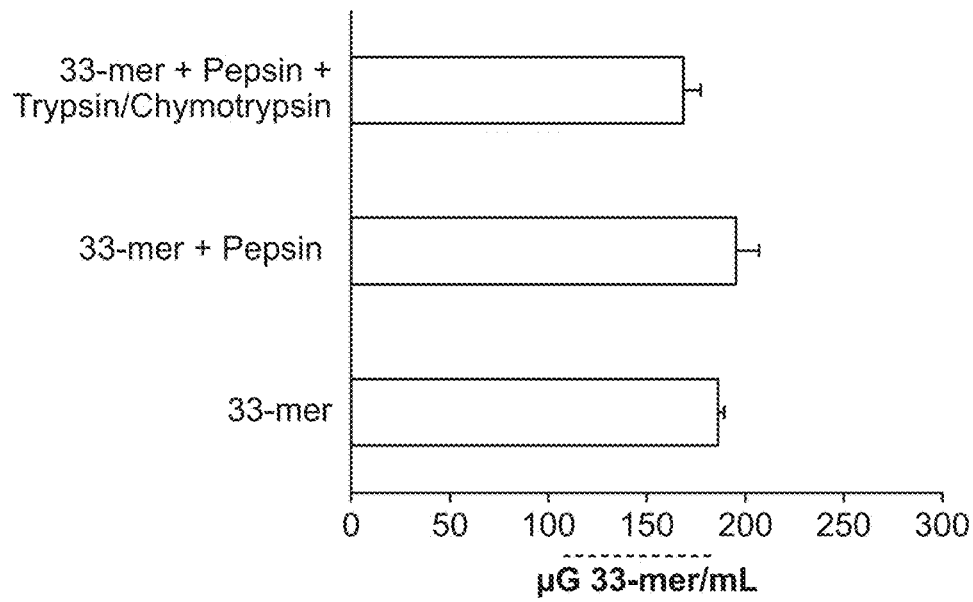
FIG. 2B
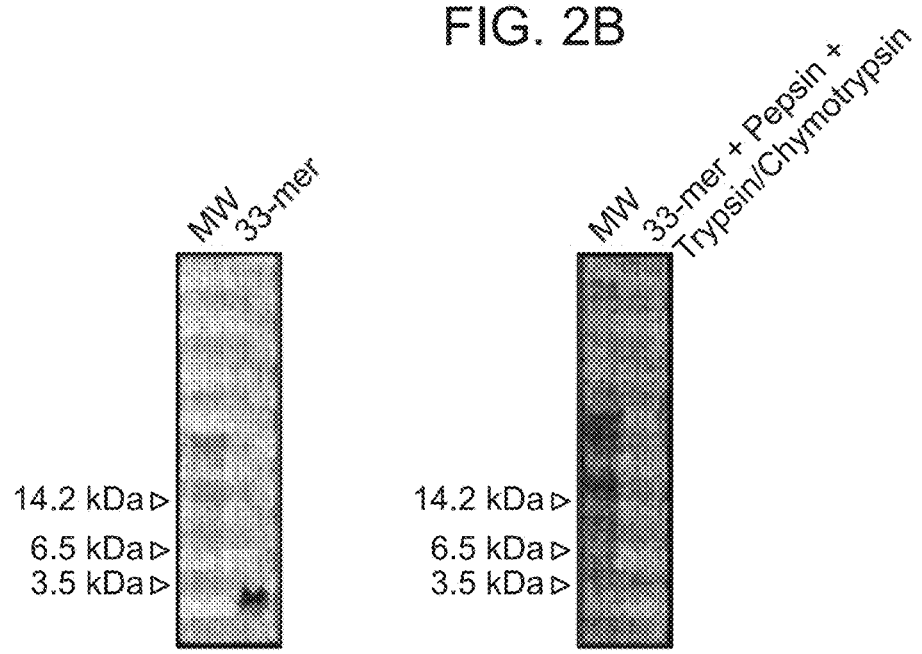
FIG. 2C

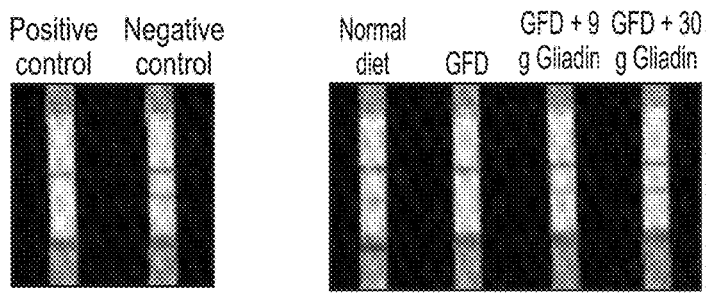
FIG. 3A
|  | Normal diet | GFD (ppm) | GFD + 9 g Gliadin | GFD + 30 g Gliadin |
|---|---|---|---|---|
| HL901 | >500 | <6 | >500 | >500 |
| HL902 | >500 | <6 | >500 | >500 |
| HL903 | >500 | <6* | >500 | >500 |
| HL904 | >500 | <6 | >500 | >500 |
| HL905 | >500 | <6 | 250-500 | >500 |
| HL906 | >500 | <6* | 250-500 | >500 |
| HL907 | >500 | <6 | >500 | >500 |
| HL908 | >500 | <6 | >500 | >500 |
| HL909 | >500 | <6 | 6-25 | >500 |
| HL910 | >500 | <6 | >500 | >500 |
| HL911 | >500 | <6 | >500 | >500 |
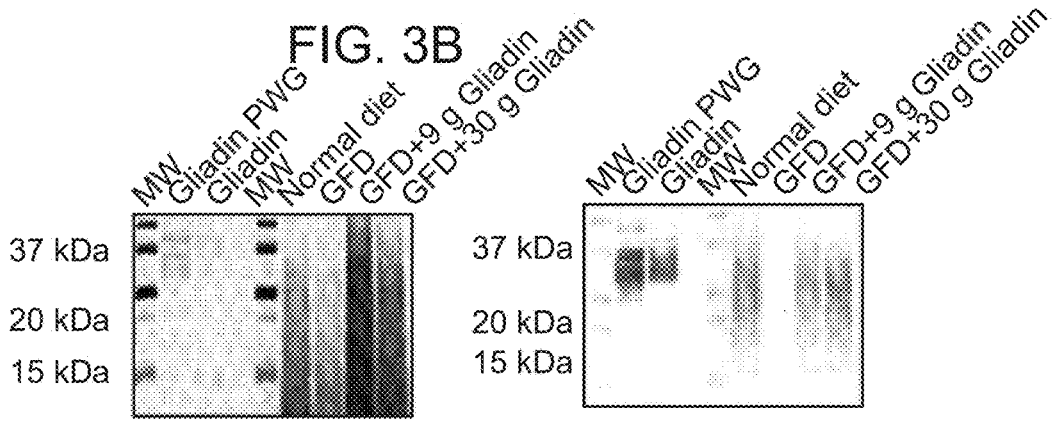
FIG. 3B
FIG. 3C
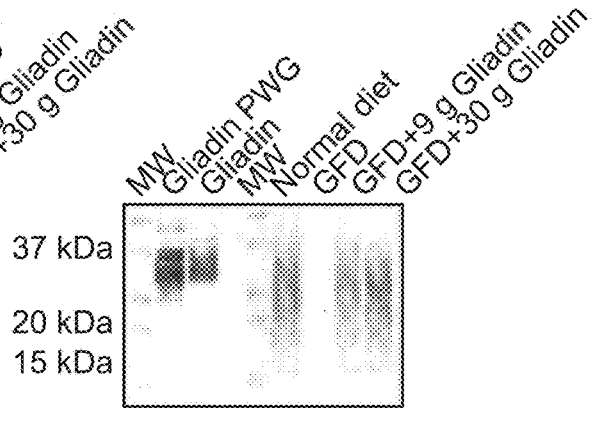
FIG. 3D

DETERMINATION OF LEVELS OF IMMUNOGENIC GLUTEN PEPTIDES IN HUMAN SAMPLES

FIELD OF THE INVENTION

The present invention fitted in the medical-clinical sector, shows a method for monitoring the ingestion of gluten by measuring protein/gluten peptides present in fecal samples with antibodies against immunogenic peptides resistant to gastrointestinal digestion. The presence or absence of these immunogenic peptides is controlled by immunological assays based on antibodies reactive against immunogenic gluten peptides that are resistant to proteolysis. These assays may be quantitative techniques ELISAs, or qualitative as rapid immunochromatographic assays, immunoblots, etc. These measures may also be applied to verify compliance with the gluten-free diet, to improve diagnosis in cases of refractory or severe symptoms of celiac disease in which a gluten-free diet is supposedly being respected, or to clinical research on the effectiveness of enzymatic therapies related with prolamin detoxification.

BACKGROUND OF THE INVENTION

Gluten is a set of storage proteins of cereals. Gluten proteins from wheat, barley, rye and probably oats, are not tolerated by genetically predisposed individuals with celiac disease (CD). In wheat, gluten is composed of an ethanol-soluble fraction (prolamins: α, β, γ and (ω-gliadins) and other insoluble, glutenins (high and low molecular weight subunits) (Wieser, 2007 Food Microbiol. 24:115-119; Fasano, 2009, Sci Am, 301:54-61). Gliadins and glutenins are also unusually rich in proline (~15%) and glutamine (~35%) residues. As a result, while most dietary proteins are digested by gastrointestinal proteases to single amino acids, dipeptides or tripeptides. gluten proteins are not completely digested (Erickson and Kim. 1990, Annu Rev Med 41: 133-139, Gray, 1991, New York: Oxford University, pp. 411-420; Ganapathy et al., 2006, Academic Press, pp. 1667-1692). Therefore, some of the gluten peptides generated during gastrointestinal digestion are highly resistant to digestion by gastric and pancreatic enzymes, so that they persist in the gut. These peptides are capable of being internalized into the intestinal cells and, therefore, glutamine residues can be deaminated by tissue transglutaminase (tTG). Genetic predisposition of individuals with CD makes them intolerant to these peptides because their immune system reacts pathologically against autoantigens generated by gluten peptides/tTG-interaction (Korponay-Szab6 et al., 2007, BMJ, 335: 1244-1247; Bethune and Khosla, 2008, PLOS Pathogens, 4: e34; Jabri and Sollid, 2009, Nat Rev Immunol., 9:858-870). Deamidated peptides induce an immune response mediated by T cells that causes chronic inflammation of the small intestine. Intestinal Villi are destroyed due to the immunological reaction, resulting in a reduction of the intestinal absorption which can lead to symptoms such as diarrhea, anemia, stunting, weight loss, bone disorders, neurological disorders, cancer, etc. (Alaedini and Green, 2005, Ann Int Med, 142:289-299; Catassi and Fasano, 2008, Curr Opin Gastroenterol., 24:687-691: Tack et al., 2010, Gastroenterol Hepatol, 7:204-213).

One of the main gluten peptides described to date is the 33-mer peptide from a2-gliadin (Shan et al., 2002. Science, 297:2275-2279, Bethune et al., 2009, Chem Biol, 16:868-881) that has been shown to be resistant to gastrointestinal digestion, substrate of the tTG mediated deamination and highly reactive with T cells isolated from celiac patients. The identification of the 33-mer peptide and other peptides, helps to demonstrate that gluten epitopes with high antigenicity are located in gliadin regions rich in proline and glutamine residues (Shan et al., 2002, Science, 297: 22752279; Tye-Din et al., 2010, Sci Transl Med 2:41 RA51).

Nowadays, the only existing therapy for patients with celiac disease is a strict gluten-free diet (GFD). Noncompliance with the GFD has been associated with osteoporosis, iron deficiency anemia, depression and infertility, all of which is improved, to some extent, by adhering to the gluten-free diet. These observations give us an idea of the importance of adherence to a GFD to reduce symptoms, prevent nutritional deficiencies and improve the quality of life of these patients. However, several studies based on intestinal biopsies have suggested that dietary transgressions are relatively frequent, being between 32.6% and 55.4% in the populations studied (Ciacci et al., 2002, Digestion, 66: 178-185; Sylvester and Rashid, 2007, Can J Gastroenterol., 21:557564). The lack of adherence to a strict gluten-free diet is the main reason for poorly controlled celiac disease in adults. [00051 In addition, there is a part of the celiac population that does not seem to respond positively to the GFD and suffer symptoms of persistent or recurrent malabsorption and intestinal villous atrophy. This population could be suspected of having refractory CD, a rare disease (approximately 5%-10% of patients with CD) that appears in patients without apparent positive response to the gluten-free diet (Al-Shot et al., 2007, Dig Dis 25:230-236, Freeman. 2009, Gut Liver, 3:237-246•, Rubio-Tapia and Murray, 2010, Gut, 59:547-557). Although this refractory disease was described in patients with assumed total absence of gluten intake, involuntary ingestion and hypersensitivity to a small amount of gluten can also trigger the symptoms of the disease. The lack of an accurate marker for monitoring compliance with the GFD is still an unresolved issue and is particularly difficult in the case of minor dietary transgressions (Fernandez-Calle et al., 1993, Gut, 34:774-777). There is no way to demonstrate gluten intake and thereby avoid possible harmful consequences. In fact, the consequences of dietary transgressions can only be measured by observing mucosal inflammation and/or villous atrophy for which intestinal biopsies would have to be performed and, as a result, the patient would have to be anesthetised with the possible consequences that this may have.

Control of anti-tTG has been proposed as a marker to assess the strict compliance with the GFD. However, the effectiveness of this marker to control the intake of gluten is not yet clear (Tack et al., 2010, Gastroenterol Hepatol., 7:204213). Other markers have been proposed for monitoring the diet, such as permeability test (Duerksen et al., 2005) or fecal calprotectin (Ertekin et al., 2010, J Clin Gastroenterol., 44:544-546). These methods can demonstrate the presence of inflammatory processes, so that if the values of these markers are altered it can be a result of infectious diseases, inflammatory bowel diseases or allergy processes, meaning that they do not need to be a measure of the direct intake of gluten. Therefore, there is no effective method to verify that the celiac patient is performing a GFD or to eliminate the possibility that the refractory CD symptoms are due to a hypersensitive intolerance to gluten traces associated with unintentional exposure to toxic cereals.

Compliance with the diet assessed by interview has been suggested as a marker of CD control for its low cost, non-invasiveness, and its proven correlation with intestinal damage. However, GFD involves numerous restrictions for patients because of its social and economic implications.

Additionally, a gluten-free diet is difficult to maintain due to the ubiquity of gluten in foods, educational misinformation, changes in food labeling and possible cross-contamination in food (Bethune et al., 2009, Chem Biol, 16:868-881; Selimoglu and Karabiter, 2010, J Clin Gastroenterol., 44:4-8). Moreover, certain lifestyles and some sectors of the population make difficult, to some extent, compliance with the GFD. Furthermore, there is no alternative to patient interviews to know how reliable the results of these clinical trials are.

A more direct measure of the ingestion of gluten could provide critical information about the patient: the detection of infringements of the GFD before anatomical damage, inadvertent consumption detection, the accuracy assessment of the adherence to treatment in the initial period after diagnosis when patients are less familiar with the diet, etc. providing an easy and reliable confirmation of the results obtained. Therefore, a sensitive and reliable marker to monitor and detect gluten intake could be a useful tool for the proper compliance with the GFD and probably for an accurate diagnosis of refractory CD.

Monoclonal antibodies (moAbs) G12 and A1 obtained against the main immunogenic epitope of a-gliadin have demonstrated to be very useful in the detection of toxic peptides in food samples as well as in clinical research of gluten enzymatic detoxification (Morón et al., 2008, Am J Clin Nutr., 87:405-414, Morón et al., 2008, PLOS ONE, 3: e2294, Ehren et al., 2009, PLOS ONE, 4: e6313, Alvine Pharmaceuticals, Inc., Biomedal SL). The sensitivity and specificity of the monoclonal antibodies and their ability to recognize peptides resistant to gastrointestinal digestion could make them ideal for monitoring immunotoxic gluten peptides obtained after intestinal digestion in human samples. Recognition epitopes from moAb G12, QP(Q/E) LP(Y/F), are present in major peptides described recently in a high throughput screening performed with 2,700 peptides from prolamins of different cereals (Tye-Din and al., 2010, Sci Transl Med 2:41 RA51). Undigested peptide fragments from gluten intake that are not absorbed could be recovered from the feces, which would demonstrate gluten intake by the individual.

In this patent, we have evaluated the feasibility of monitoring gluten, intact and digested. In the feces by the detection of epitopes associated with the 33-mer peptide, which could be used in clinical studies and dietary monitoring, as well as in the diagnosis of refractory CD.

DESCRIPTION OF THE INVENTION

The gluten-free diet is the only effective treatment today for celiac disease. Therefore, compliance with GFD should be monitored to prevent cumulative direct and indirect damage, as well as to confirm the persistence of any symptom of celiac disease is not due to a transgression (intentionally or not) of the diet. However, currently there are no methods to monitor dietary compliance in patients with celiac disease.

The aim of the present invention is the application of immunological methods for monitoring compliance with the gluten-free diet by detecting immunotoxic peptides present in feces that are resistant to gastrointestinal digestion. It is an object of the invention the application of immunological techniques based on antibodies that recognize immunogenic peptides from gluten that resist gastrointestinal digestion. Preferably, the invention employs immunological techniques using antibodies recognizing the 33-mer peptide from gliadin. A preferred way of making the detection of peptides is by rapid qualitative methods based on immunochromatographic strips or by quantitative and automated methods as ELISA techniques. The preferred method used in the invention should be able to detect gluten ingested equivalent to 50 mgs of wheat gluten per day, which is the maximum amount described for a gluten free diet, or at least 20 ppms of gluten equivalent in feces.

It is also an object of the present patent kits or immunological analytical devices based on antibodies reactive against the 33-mer from gliadin that are suitable for the detection of gluten peptides in feces.

These procedures and analytical kits are also an object of this patent because of its use to reveal a lack of adherence to GFD, either due to contamination of food consumed or to a voluntary/involuntary occasional intake of foods containing gluten. Furthermore, it is object of the present invention the application of the detection of these immunotoxic peptides in feces for the clinical research control on celiac disease, including enzymatic therapies related to gluten prolamins detoxification, seize of immunotoxic peptides and other alternative therapies.

The object of the present invention is a process for detecting or monitoring the gluten ingested by detecting immunotoxic peptides in feces, characterized by the use of immunological methods using antibodies that recognize preferably epitopes related to 33-mer gliadin peptide and other peptide sequences resistant to gastrointestinal digestion. Thus, in one aspect, the invention defines a process for monitoring gluten consumption in an individual comprising detecting gluten immunogenic peptides in fecal samples by immunological methods using antibodies that recognize peptides from gluten proteins resistant to gastrointestinal digestion.

It is an object of the present invention the use of immunological techniques for such gluten monitoring, immunological methods such as indirect ELISA, competitive ELISA, sandwich ELISA, immunochromatographic strips, fluorescent immunomicroparticles, Western blot, biosensors based on electrochemical reactions catalyzed by enzymes attached to the antibodies, by magnetic particles coated with antibodies, by surface plasmon resonance, and other techniques in which an analyte bound to an antibody is detected.

In a preferred embodiment of the invention, these methods are characterized by the preferred use of one or more monoclonal antibodies capable of detecting epitopes contained or similar to peptide 33-mer (SEQ ID NO: 1), such as the following sequences: SEQ ID NO. 2, SEQ ID NO, 3. SEQ ID NO: 4, SEQ ID NO: 5, SEQ ID NO: 6, SEQ ID NO: 7, SEQ ID NO: 8. In a particular embodiment, the process for monitoring the ingested gluten in which the immunological methods use at least a monoclonal antibody with ability to detect epitopes contained in a 33-merpeptide SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8.

In a preferred embodiment of the invention the antibodies used for immunological techniques would be G12 and A1 because of the proven relation between its reactivity and the potential immunotoxicity of a sample. The invention also contemplates the use of the antibody R5 that reacts with the epitope SEQ ID NO: 9, which also can be found in gluten peptides resistant to gastrointestinal digestion, but with less specificity against immunogenic peptides resistant to proteases. Thus, in another particular embodiment, the process for monitoring the ingested gluten in which the immunological methods use at least one of the monoclonal antibodies selected from the list consisting of antibody G12, antibody A1 and antibody R5.

A preferred embodiment of the invention would be the use of immunological methods based on G12 monoclonal antibody conjugated to an enzyme that allows a quantitative assay using chromogenic, luminescent or fluorogenic substrates, this procedure would use a standard of gliadin, hydrolysed gliadin, complete 33-mer peptide or a part of its sequence of at least 6 amino acids (SEQ ID NO: 2). Thus, in a particular embodiment, the process for monitoring the ingested gluten according to claim 1 in which the immunological methods are an indirect ELISA, a competitive ELISA, a sandwich ELISA, immunochromatographic strips, fluorescent immunomicroparticles, magnetic immunoparticles, Western blot, electronic biosensors or resonance biosensors. In another particular embodiment, the immunological methods use a monoclonal antibody G12 conjugated to an enzyme that allows a quantitative assay using chromogenic, fluorogenic or luminescent substrates.

Another object of the invention is constituted of the particular use of immunochromatographic strips based on the anti-33-mer from gliadin antibodies, G12 and A1 which allow a rapid and semiquantitative detection of proteins/peptides from gluten content in feces. Thus, in a particular embodiment, the immunological methods use at least one of anti-gliadin antibodies, G12 and A1, for carrying out a semiquantitative assay based on immunochromatographic strips of rapid detection.

The invention proposes a measure of the gluten ingested by the individual through the diet. This is a useful process for the control of the gluten ingested by using analytical methods in which a correlation between the quantity of ingested gluten and the estimated quantity of gluten protein/peptides in feces obtained from these methods has been shown.

The invention proposes an analytical instrument for monitoring compliance with the GFD, as well as to discard uncontrolled intake of gluten in patients suspected of suffering from the called refractory celiac disease. Also, with this procedure, new therapeutic alternatives for enzymatic detoxification of gluten and other alternative therapies may also be controlled in the feces of celiac patients subjected to clinical trials or therapeutic prescription in the future. since the effectiveness of the therapy could be determined by measuring the presence or absence of peptides in feces after 12-48 hours from the intake of a controlled amount of gluten in conjunction with therapies to eliminate immunotoxic peptides.

Some issues that are not still resolved in clinical practice, such as the control of the GFD or the control of involuntary exposure to gluten due to food contamination, could be resolved with simple immunological assays in feces. Medics, clinicians and analysts might consider these methods useful for clinical trial design and monitoring of their celiac patients to establish consistent conclusions on the state of the patient's disease. Extraction of the peptides from the feces can be carried out directly with a hydroalcoholic solution of 40 to 60%. Sometimes, due to the nature of the food ingested, the gluten extraction from the feces could be improved by adding a solution containing dispersing agents such as guanidinium chloride, arginine chloride, etc., or detergents such as polyvinylpyrrolidone, and reducing agents such as b-mercaptoethanol, DTT or TCEP.

Subsequently extracted gluten polypeptides are diluted in a buffered saline solution and are then used to make the measurement with an ELISA, either competitive or sandwich if an idea of the concentration of reactive peptides is to be obtained. The standard curve could be done with standard gliadin digested by trypsin and pepsin to simulate gastric digestion. Synthesized polypeptide reacting with the antibodies could also be used directly, preferably 33-mer from gliadin or fragments thereof with the option of making some specific modifications that retain reactivity against the antibodies. For example, the peptides that may be used for antibody G12 are the following: SEQ ID NO: 1, SEQ ID NO: 2, SEQ ID NO: 3, and SEQ ID NO: 4. For A1, besides 33-mer, the following peptides could be valid to make the standard curve with a competitive ELISA: SEQ ID NO: 5, SEQ ID NO: 6, SEQ ID NO: 7 or SEQ ID NO: 8. Thus, in a particular embodiment, the process for monitoring of ingested gluten is characterized by using as a reference standard the peptides SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO 8.

For a qualitative assay in which it is seen if the value of gluten polypeptides in feces is greater or less than a certain amount, immunochromatographic strips or ELISAs assays, using antibody G12 or A1 or both, could be used. The procedure could be carried out with a kit that contained the extraction solution of the polypeptides in feces: a reference pattern with gluten polypeptides hydrolysed by pepsin and trypsin or synthesized: and the components of an ELISA with a multiwell plate and using the antibodies A1 and/or G12 to immobilize the wells and/or for the development of the assay or immunochromatographic strips.

Therefore, in view of the foregoing, the present invention relates to a process for monitoring gluten consumption in an individual following gluten free diet comprising (a) isolating a fecal sample from said individual;
(b) treating the fecal sample of step (a) with a hydroalcoholic solution, the treating of the fecal sample providing extracted immunotoxic gluten peptides;
(c) contacting the extracted peptides of step b) with at least one monoclonal antibody which specifically binds the gluten immunotoxic peptides and with capacity of detecting at least 6 µg gluten/g of fecal sample, the contacting of the extracted peptides with the at least one monoclonal antibody forming monoclonal antibody-gluten peptide complexes; and
(d) detecting the monoclonal antibody-gluten peptide complexes formed in step (c); wherein the detection of the monoclonal antibody-gluten peptide complexes is indicative that the individual has consumed gluten.

Likewise, in another aspect, the present invention relates to a process for monitoring the effectiveness of therapies related to the elimination of immunogenic peptides of gluten comprising (a) isolating a fecal sample from said individual;
(b) treating the fecal sample of step (a) with a hydroalcoholic solution, the treating of the fecal sample providing extracted immunotoxic gluten peptides;
(c) contacting the extracted peptides of step b) with at least one monoclonal antibody which specifically binds the gluten immunotoxic peptides and with capacity of detecting at least 6 µg gluten/g of fecal sample, the contacting of the extracted peptides with the at least one monoclonal antibody forming monoclonal antibody-gluten peptide complexes; and
(d) detecting the monoclonal antibody-gluten peptide complexes formed in step (c); wherein the detection of the monoclonal antibody-gluten peptide complexes is indicative that the therapies related to the elimination of immunogenic peptides are effective.

In a particular embodiment of both processes, the monoclonal antibody specifically binds the gluten immunotoxic peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

In another particular embodiment of both processes, the monoclonal antibody is selected from the group consisting of antibody G12, antibody A1 and antibody R5.

In another particular embodiment of both processes, step c) is carried out by an indirect ELISA, a competitive ELISA, a sandwich ELISA, immunochromatographic strips, fluorescent immunomicroparticles, magnetic immunoparticles, Western blot, electronic biosensors or resonance biosensors.

In another particular embodiment of both processes, step d) comprises detecting the complex by means of a reference standard using the peptides SEQ ID NO: 1, SEQ ID NO: 2, SEQ ID NO: 3, SEQ ID NO: 4, SEQ ID NO: 5, SEQ ID NO: 6, SEQ ID NO: 7 or/and SEQ ID NO 8.

In another particular embodiment of both processes, the process further comprises providing a kit comprising:
  the hydroalcoholic solution of step b),
  a reference peptide standard comprising at least one immunogenic peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, and
  the at least one monoclonal antibody of step c).

Likewise, in another aspect, the invention relates to a process for monitoring the compliance with gluten free diet comprising detecting immunotoxic peptides in fecal samples by immunological methods using antibodies that recognize peptides from gluten proteins resistant to gastrointestinal digestion, wherein the detection of immunogenic peptides in said samples indicate the non-compliance of the individual with the gluten-free diet.

In another aspect, the invention relates to a process for detecting the uncontrolled intake of gluten in celiac patients following a gluten-free diet but with refractory and acute symptoms of celiac disease comprising detecting immunotoxic peptides in fecal samples by immunological methods using antibodies that recognize peptides from gluten proteins resistant to gastrointestinal digestion, wherein the detection of immunogenic peptides in said samples indicate the uncontrolled intake of gluten in celiac patients.

In another aspect, the invention relates to a process for monitoring the effectiveness of therapies related to the elimination of immunogenic peptides of gluten comprising detecting immunotoxic peptides in fecal samples by immunological methods using antibodies that recognize peptides from gluten proteins resistant to gastrointestinal digestion, wherein the detection of immunogenic peptides in said samples indicate that the therapies are effective.

In a particular embodiment, the immunological methods use at least one monoclonal antibody with reactivity against a 33-mer peptide SEQ ID NO: 1.

In another particular embodiment, the immunological methods use at least a monoclonal antibody with ability to detect epitopes contained in a 33-mer peptide SEQ ID NO: 1, SEQ ID NO: 2, SEQ ID NO: 3, SEQ ID NO: 4, SEQ ID NO: 5, SEQ ID NO: 6, SDQ ID NO: 7 or SEQ ID NO: 8.

In another particular embodiment, the immunological methods use at least one monoclonal antibody with reactivity against a 33-mer peptide SEQ ID NO: 1, In another particular embodiment, the immunological methods use at least a monoclonal antibody with ability to detect epitopes contained in a 33-mer peptide SEQ ID NO: 1, SEQ ID NO. 2, SEQ ID NO: 3, SEQ ID NO: 4, SEQ ID NO: 5, SEQ ID NO: 6, SEQ ID NO: 7 or SEQ ID NO: 8.

In another aspect, the present invention relates to an analytical kit for detecting immunogenic gluten peptides in feces containing: a solution for the extraction of gluten in feces, a reference peptide standard comprising at least part or all of a 33-mer immunogenic peptide from gliadin, and an immunoassay using an antibody reactive against the 33-mer peptide from gliadin.

In a particular embodiment, the solution for the extraction of gluten in feces is an aqueous solution having in its composition any of the following components: a dispersing agent, a mild detergent, a reducing agent, a buffer, and ethanol, the reference peptide standard is obtained by hydrolysis with pepsin and trypsin of gliadin or a synthetic peptide comprising part or all of the sequence of the 33-mer peptide from gliadin, and the immunoassay using an antibody reactive against the 33-mer peptide from gliadin is selected from ELISA, immunochromatographic strips, immunoblots, and electronic biosensors.

In a particular embodiment of the kit, the immunological methods use at least one monoclonal antibody with reactivity against a 33-mer peptide SEQ ID NO: 1.

In another particular embodiment of the kit, the immunological methods use at least a monoclonal antibody with ability to detect epitopes contained in a 33-mer peptide SEQ ID NO: 1, SEQ ID NO. 2, SEQ ID NO: 3, SEQ ID NO: 4, SEQ ID NO: 5, SEQ ID NO: 6, SEQ ID NO: 7 or SEQ ID NO: 8.

FIGURE LEGENDS

To complement the description being made and in order to aid a better understanding of the characteristics of the invention, according to a preferred practical embodiment thereof, it is attached as an integral part of said description, with illustrative and not limiting character, the following figures:

FIG. 1. Relative affinity of moAb G12 to immunotoxic peptides derived from PWG gliadin after simulating gastrointestinal digestion. A and B. SDS-PAGE and Western blot of PWG gliadin, PWG gliadin+pepsin and PWG gliadin+pepsin+trypsin/chymotrypsin. Samples were stained with silver or transferred to a PVDF membrane with moAb G12. MW: molecular weight marker. C. Analysis by competitive ELISA 2-HRP of peptides from gliadin PWG.

FIG. 2. Resistance of 33-mer peptide to be broken by gastrointestinal enzymes. A. Amino acid sequence of 33-mer peptide. The recognition sequence of moAb GI 2 into the 33-mer peptide is in bold. B. Competitive ELISA for the detection of 33-mer after treatment with pepsin, trypsin and chymotrypsin using the moAb G12-HRP. C. Western blot of 33-mer peptide after treatment with gastrointestinal enzymes. M\V: molecular weight marker. Two separate assays with 3 replicates each one were carried out.

FIG. 3. Gluten detection in feces from healthy individuals subjected to a gluten-controlled diet. A and B. Gluten peptides/proteins semiquantification in feces of healthy individuals (n=11) by immunochromatographic strips G12. The upper line is a positive internal control indicates that the device has worked correctly, and bottom line indicates the presence of gluten. HL901-HL911: subjects who participated in the study. *Gluten traces were detected. C and D. SDSPAGE and Western blot of gluten peptides and proteins extracted from the feces. MW: molecular weight marker.

Figure 4:
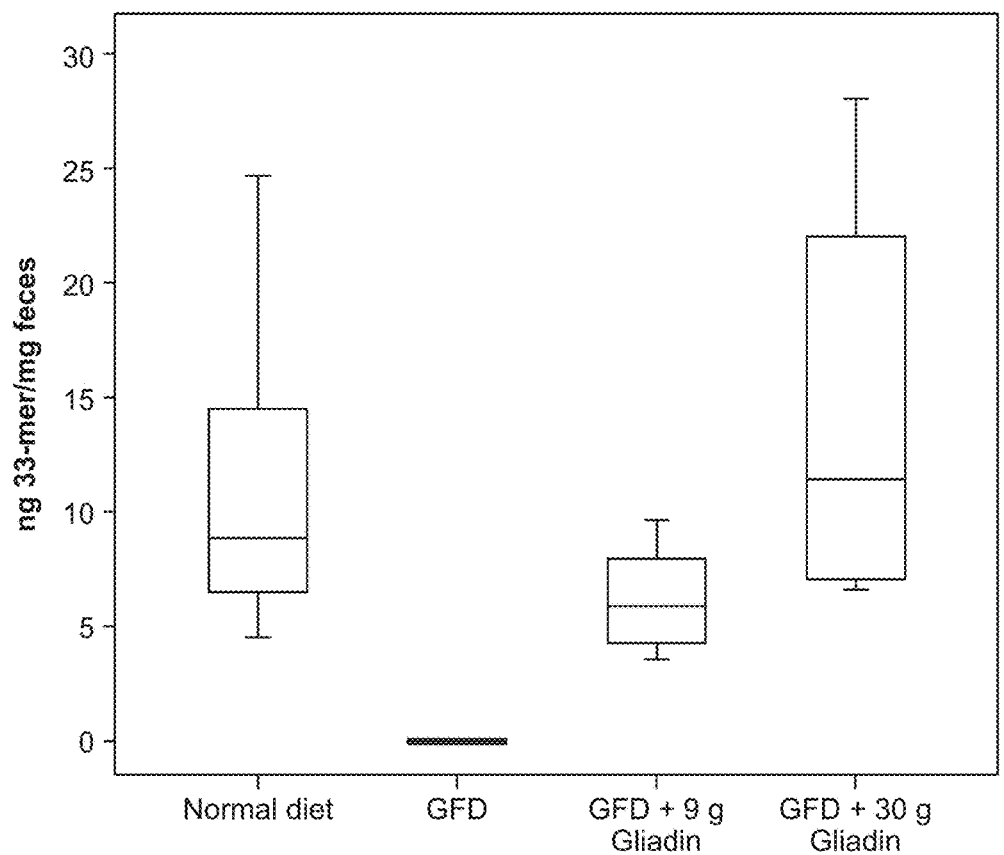

FIG. 4. Concentration of 33-mer peptide (ng/mg) in feces after a gluten-controlled diet. Competitive ELISA GI2HRP to determine the relationship between gluten proteins ingested/excreted by its content in 33-mer peptide. The concentration of 33-mer peptide was determined by a standard curve of 33-mer. Two separate tests were carried out, each with three replicates.

Figure 5:
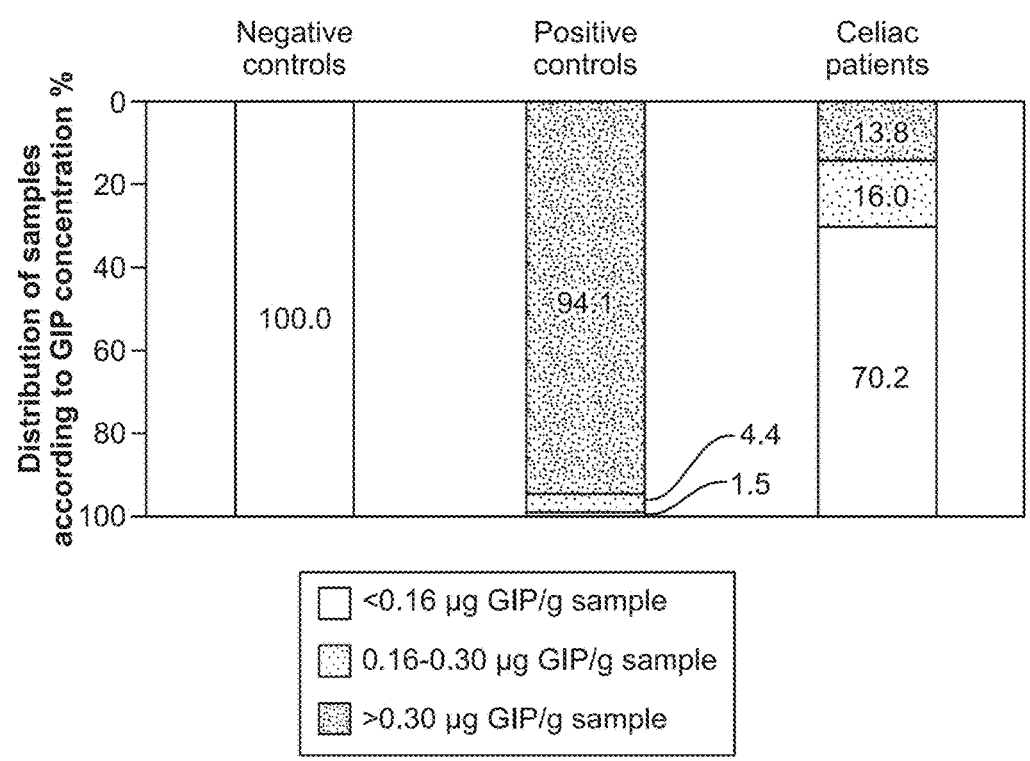

FIG. 5. Percentage distribution of controls and GFD-treated celiac patients according to GIP concentration. Celiac patients (n=188) were children and adults on GFD for ≥1 year and healthy controls (n=84) were classified into positive controls (children and adults on a gluten containing diet, n=73); and negative controls (babies between 0 and 8 months of age who were only fed GFD formula milk, n=11). GIP, gluten immunogenic peptides; GFD, gluten free diet.

Figure 6:
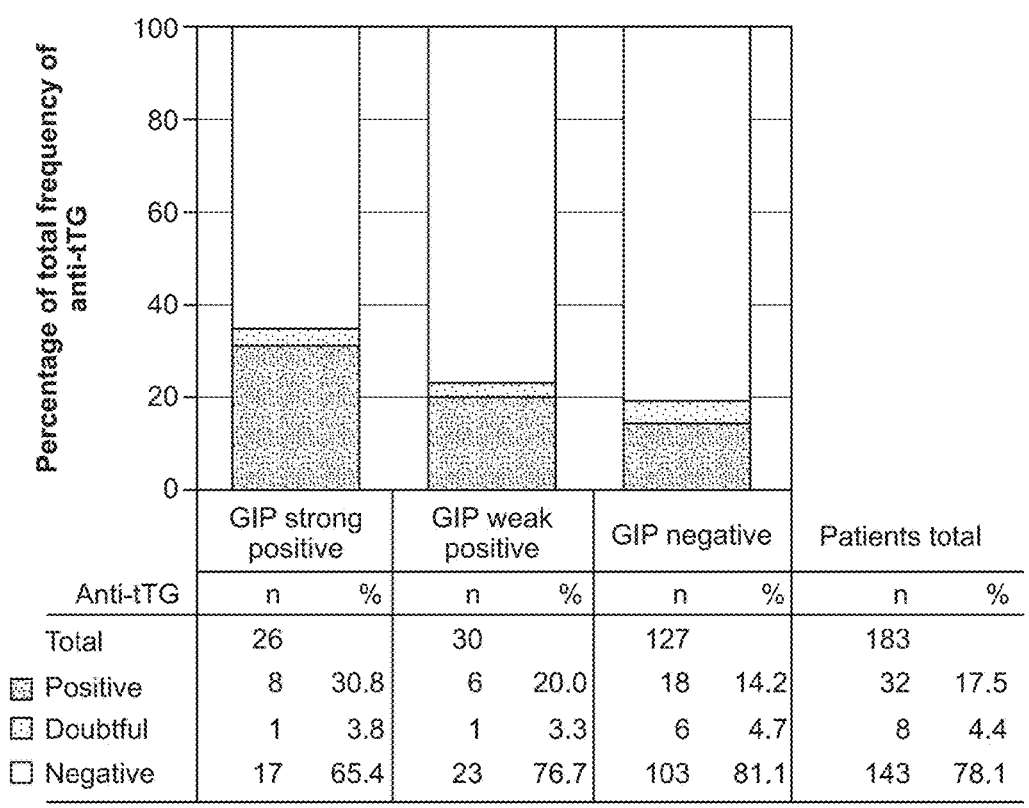

FIG. 6. Evaluation of GFD adherence in celiac patients according to serological anti-tissue transglutaminase antibody levels and association with fecal GIP content. Correlation between anti-tTG-IgA and fecal GIP. GIP content was divided into three groups according to GIP titres by ELISA: positive (>0.30 μg GIP/g feces), weak positive (0.16 and 0.30 μg GIP/g feces) and negative (<0.16 μg GIP/g feces). Levels of anti-tTG-IgA are expressed as EliA U/ml and classified as positive (>10 EliA U/ml), indeterminate (7-10 EliA U/ml) and negative (<7 EliA U/ml). Anti-tTG, anti-tissue transglutaminase antibody; GFD, gluten-free diet; GIP, gluten immunogenic peptides.

Figure 7:
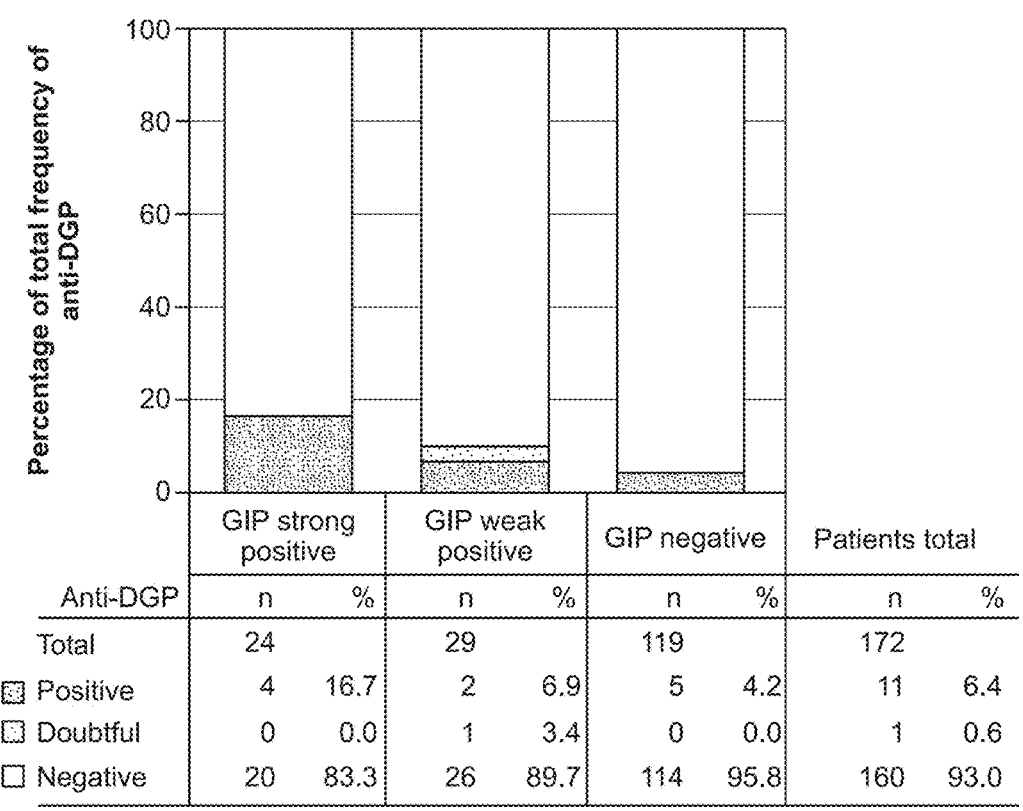

FIG. 7. Evaluation of GFD adherence in celiac patients according to serological antideamidated gliadin peptide antibody levels and association with fecal GIP content. Correlation between anti-DGP-IgA and fecal GIP. GIP content was divided into three groups according to GIP titres by ELISA: positive (>0.30 μg GIP/g feces), weak positive (0.16 and 0.30 μg GIP/g feces) and negative (<0.16 μg GIP/g feces). Levels of anti-DGP-IgA are expressed as EliA U/ml and classified as positive (>10 EliA U/ml), indeterminate (7-10 EliA U/ml) and negative (<7 EliA U/ml). Anti-DGP, antideamidated gliadin peptide antibody; GFD, gluten-free diet; GIP, gluten immunogenic peptides.

Figure 8:
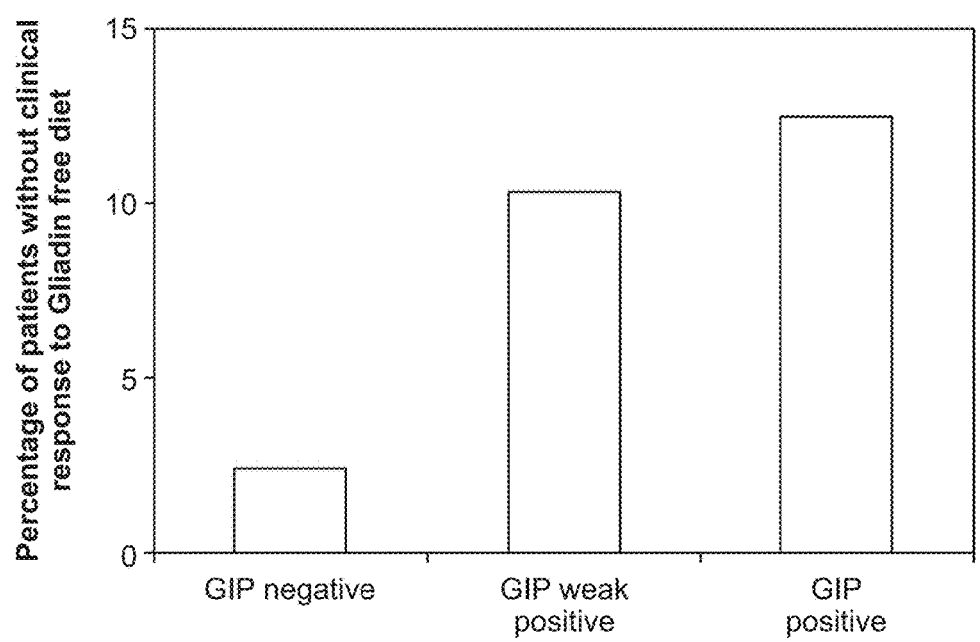

FIG. 8. Percentage of patients that reported symptoms despite being on a GFD for at least 12 months by GIP content in stools. GIP, gluten immunogenic peptides; GFD, gluten free diet; GIP Positive (>0.30 μg GIP/g feces); GIP Weak positive (0.16-0.30 μg GIP/g feces); GIP Negative (<0.16 μg GIP/g feces).

PREFERRED EMBODIMENT OF THE INVENTION

EXAMPLE 1

Quantification of Toxic Peptides from Gliadin PWG Obtained after Simulated Gastrointestinal Digestion The present example shows that a substantial portion of the immunogenic peptides of gluten remain susceptible for fecal detection despite gastrointestinal digestion. Among the major proteins of the diet, those that constitute gluten are the only ones that contain approximately 15% of proline residues and 35% of glutamine residues. The high content of these two amino acids prevents the complete proteolysis of these proteins by gastric and pancreatic enzymes, so that peptide fragments are formed in the small intestine which are immunotoxic for celiac patients. In particular, the 33-mer peptide was found as one of the main contributors to the immunotoxicity of gluten (Shan et al. 2002, Science, 297: 2275-2279). This peptide of the a-2 gliadin contains six recognition epitopes for T cells and is highly resistant to proteolysis.

The moAb G12 is specific for the epitope of six amino acids SEQ ID NO: 10, with 3 repetitions in the 33-mer peptide. Moreover, this antibody is capable of recognizing other immunoreactive peptides present in gliadin and other toxic prolamins. The purpose of this example is to know the capacity of G12 antibody to detect toxic peptides formed after gastrointestinal digestion simulation of gliadin. For standardization of the assay PWG gliadin was used, considered an international reference reagent in gluten analysis due to its high content of gliadins, good solubility, homogeneity, stability and for being constituted of 28 wheat European cultivars (Eckert et al., 2006, J Cereal Sci, 43:331-341).

Gliadin was subjected to sequential digestion with pepsin (main protease present in the stomach), trypsin and chymotrypsin (proteases contained in the intestinal membrane). The samples were incubated at 37° C. in HCl solution (pH 2) containing 0.06 mg/mL of pepsin. Samples were incubated for 60 minutes and inactivated by heating at 95° C. for 5 minutes. After simulating gastric digestion with pepsin, the digestions were adjusted to pH 6.0 with sodium phosphate buffer, and incubated with pancreatic proteases: trypsin (0.375 mg/mL) and chymotrypsin (0.375 mg/mL). After the duodenal simulation at 37% for 30 minutes the samples were immediately inactivated at 95° C. for 5 minutes.

The proteic profile of the prolamins fractions which constitute PWG gliadin was analyzed by SDS-PAGE to observe the pattern of bands obtained after the enzymatic treatment and to confirm that samples had been digested. For the analysis by SDS-PAGE, the samples were diluted in running buffer (62.5 mM Tris-HCl pH 6.8, 10% glycerol, 2% SDS, 0.001% bromophenol blue and 5% 2-mercaptoethanol) and denatured by boiling at 100° C. for 5 minutes. This step was repeated a total of three times. Samples were run on 15-18% polyacrylamide gels (SDS-PAGE) at a constant voltage of 100 V using MiniProtein system (Bio-Rad Laboratories). The separated proteins in the electrophoresis gel were stained using silver staining.

The intact PWG gliadin evaluated by ID gel revealed intense bands of alpha, beta and gamma gliadin (MW=33-45 kDa) and weak bands of omega gliadin (MW=50-67 kDa) (Eckert et al., 2006 J Cereal Sci, 43:331341). Digestion of these proteins mediated by pepsin (gastric digestion) resulted in the formation of smaller peptide fragments below 25 kDa. Sequentially, trypsin and chymotrypsin digestion generated smaller peptides (less than 15 kDa), resulting from the hydrolysis process mediated by these enzymes (FIG. 1A).

In order to verify whether PWG gliadin peptides obtained by the process of gastrointestinal digestion were recognized by the anti-33-mer antibody, a Western blot with this antibody was carried out for the samples described above: undigested PWG gliadin, PWG gliadin after gastric digestion and PWG gliadin after intestinal digestion (prior gastric digestion). Protein extracts initially obtained were separated by SDS-PAGE and then incubated with G12 antibody onto PVDF membranes. After that, the samples were incubated in blocking buffer (TBS with 5% skim milk) overnight, after G12 antibody was added (1:5000 dilution in blocking solution). After 3 washes, membranes were incubated with secondary antibody anti-mouse IgG conjugated to phosphatase (Sigma, St. Louis, Mo.) (1:2000 dilution in blocking solution). The membrane was developed using Sigma-Fast system.

Figure 1B:
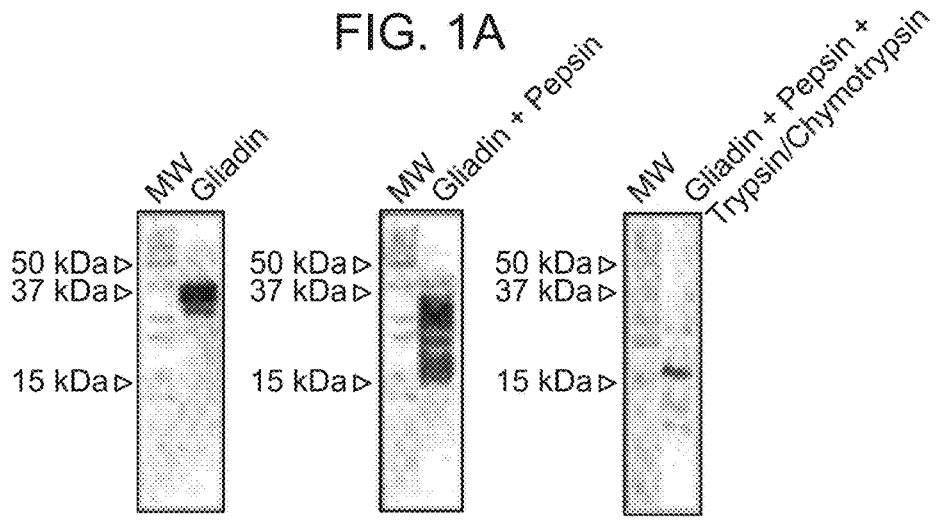

The G12 antibody was able to recognize the different factions into PWG gliadin. After gastric digestion, peptide fragments formed remained being recognized by the G 12 antibody (FIG. 1B). Sequential treatment with pancreatic enzymes (trypsin, chymotrypsin) resulted in the presence of smaller peptides also recognized by moAb G12.

In order to determine the capacity of the G12 antibody to quantify the toxic peptides generated, the concentration of 33-mer and analogues peptides obtained after gastrointestinal simulation of PWG gliadin was determined by competitive ELISA also using the G12 antibody. The competitive ELISA is a very suitable technique to monitor gluten digestion since it is capable of detecting both intact proteins and small protein fragments: the latter could be underestimated by sandwich ELISA, because the detection of antigens requires at least two different epitopes on the peptide molecule.

The relative amount of immunotoxic epitopes contained in the samples was quantified by competitive ELISA using moAb G12-HRP (Biomedal SL, Seville, Spain). Maxisorp microtiter plates were used for this assay (Nunc, Roskilde, Denmark), which were coated with 100 PL/well of Sigma gliadin solution (5 ng/mL) in 0.1 M PBS ($Na_2CO_3$-NaHC03, pH 9.6), and incubated at 4° C. overnight. The plates were washed with PBS 0.05% Tween® 20 and blocked with blocking solution (PBS, 5% skimmed milk) for 1 h at room temperature. Serial dilutions of the standard (gliadin or 33-mer peptide) and samples studied were made in PBS with 3% BSA (100 μL) and 100 μL of moAb G12 conjugated to HRP solution was added to each one (1:10,000 in PBS with 3% BSA). Samples were pre-incubated 1 hour at room temperature with gentle agitation, and then added to the wells. After 30 minutes of incubation, samples were washed, and 100 PL/well of substrate solution was added (TMB, Sigma, St. Louis, Mo., USA). After 30 minutes incubation at room temperature in darkness, the reaction was stopped with 1M sulfuric acid (100 PL/well), and absorbance was measured at 450 mn (UVM340 microplate reader, Asys Hitech GMBH, Eugendorf, Austria). Gliadin/33-mer concentration was determined using the 4-parameter model.

Figure 1C:
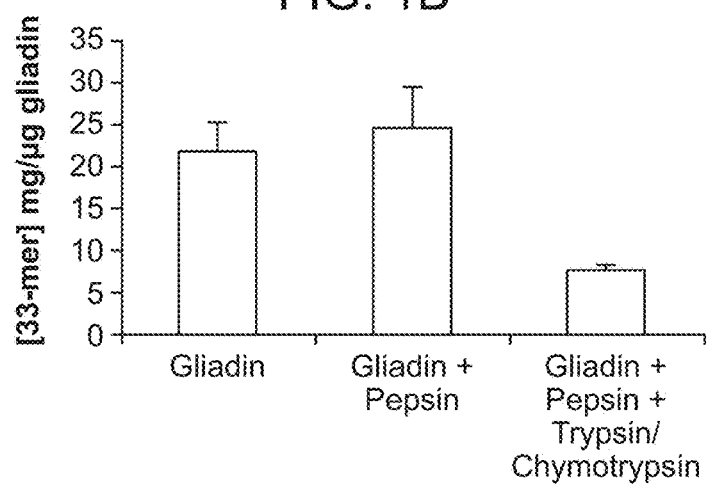

The concentration of 33-mer both in intact PWG gliadin and subjected to gastric and intestinal digestion was determined by this method. Gastric digestion of PWG gliadin resulted in a slight increase in the levels of toxic peptide. This increase is probably due to the opening of the molecules constituting the gliadin fractions so that the epitopes of anti-33-mer present are more accessible, and thus, can be identified with greater specificity [intact PWG gliadin (21.6 ng of 33-mer/μg) vs. PWG gliadin after gastric digestion (24.5 ng of 33-mer/μg)]. After the following process of intestinal digestion, the moAb G12 continued to recognize the PWG gliadin peptides formed, although with less extent (7.5 ng 33-mer/ μg) (FIG. 1C).

In contrast to these results, both in vitro and in vivo studies made with the 33-mer peptide demonstrate the great stability of this peptide to rupture by gastric, pancreatic and intestinal endoproteases. Its features make it to be suggested as the main promoter of the inflammatory response to gluten in celiac patients (FIG. 2A) (Shan et al., 2002, Science, 297: 2275-2279, 2005. J Proteome Res 4: 1732-1741).

To verify that the 33-mer peptide remains intact after gastric proteolysis (mediated by pepsin) and sequential intestinal proteolysis (mediated primarily by trypsin and chymotrypsin) an in vitro simulation of gastrointestinal digestion of this peptide was performed. The concentrations of 33-mer peptide obtained after each of the digestion processes were determined by competitive ELISA using the anti-33-mer monoclonal antibody. The concentration of 33-mer obtained after gastric digestion did not differ significantly with respect to the non-digested peptide (194 μg/mL vs. 186 μg/mL, respectively, p=0.4469). Equally, exposure of the 33-mer to the enzymes trypsin and chymotrypsin (intestinal digestion), did not change the levels of this peptide in comparison with untreated peptide (169 μg/mL vs. 186 μg/mL, respectively, p=0.1024) (FIG. 2B). These results confirm the high stability of the 33-mer to hydrolysis by enzymes involved in the digestive process.

The results obtained by ELISA were confirmed by Western blot analysis. Tricine-SDS-PAGE and Western blot were performed under standard conditions (Sousa et al., 2001, Mol Cellular Biol, 7:204-213). The immunoblotting showed bands of approximately 3.5 kDa in the sample containing unprocessed 33-mer as well as in that containing 33-mer subject to gastrointestinal digestion (theoretical 33-mer molecular weight 3.9 kDa, PIR, Protein Information Resource, Georgetown University Medical Center, USA) (FIG. 2C).

Similarly, the ability of moAb G12 to detect hydrolysates was assessed using a system for rapid detection of gluten, immunochromatographic strips based on G12 moAb (GlutenTox stick, Biomedal S.L.). The detection limit for gliadin and hydrolyzed gliadin was 30 ng/ml (6 ppm of gluten or 6 μg gluten/g of feces, see FIG. 3A, column GFD) and 50 ng/ml (10 ppm of hydrolyzed gluten), respectively, while for the 33-mer peptide and 33-mer peptide after digestion was 0.5 ng/mL in both cases. These results suggest that the analysis method is highly sensitive for both the intact proteins/peptides and their respective hydrolysates.

The results obtained by Western blot, competitive ELISA and immunochromatographic strips suggest that anti33-mer G12 antibody could be used to monitor the presence of toxic gliadin peptides and other gluten prolamins during the digestive process. At least one third of peptides reactive for G12 remained resistant to gastrointestinal digestion. Therefore, a substantial portion of prolamins epitopes of ingested food that were detected with moAb G12 may be resistant to gastrointestinal digestion and their detection may be appropriate in the gastrointestinal tract.

EXAMPLE 2

Detection and Semiquantification of Gluten Proteins/Peptides in Feces of Healthy Individuals Undergoing Gluten Controlled Diet The present example shows how the digestion that gluten proteins suffer in vivo in healthy individuals occurs, and also to determine the ability of moAb GI 2 to detect these proteins/peptides excreted through the feces. An assay was carried out in which the type and quantity of gluten consumed in healthy individuals was controlled (n-II. 7 men and 4 women, mean age 24-42 years). The inclusion criteria were the absence of diseases, gastrointestinal symptoms, medications, antibiotics in the last two months and no family history of CD. All participants were assessed for CD, showed normal serum tTG levels and HLA-DQ phenotype was not DQ-2/-8. Hemoglobin levels and blood biochemical analysis, including kidney and liver tests were within normal values. The local ethic committee from "Hospital Universitario de Leon" approved this study and informed consent was obtained from the subjects.

For this study the following protocol was adopted:

Diet:

The subjects were instructed to follow a diet in which the type and amount of gluten consumed was controlled within 15 days of this study. First, the subjects consumed a strict gluten-free diet for a week. The following 4 days, 9 g of unprocessed gluten were ingested, distributed in three meals a day. In the last 4 days, the dose was increased to 30 g of gluten, similarly distributed.

Fecal Sampling:

Fresh feces were collected from 11 subjects who participated in the study under different diet conditions: normal diet, GFD, GFD+9 g of gluten and GFD+30 g of gluten. The sampling was made before GFD and after each of the diets tested. All samples were homogenized and aliquoted within 3 hours after defecation.

The Extraction of Prolamins from Feces and Gliadin Solution:

Prolamins were extracted by mixing 1 g of feces with 10 mL of ethanol 60% (v/v) on a rotary shaker for 1 hours at room temperature. The suspension was centrifuged at 13,000×g for 10 minutes and the supernatant was removed. The positive control, PWG gliadin, was also prepared in ethanol 60% (v/v) at 1 mg/mL.

First, fecal samples was collected from individuals analyzed, who maintained a normal diet in which gluten was present (bread, pasta, cookies, etc.). The presence of gluten polypeptides in fecal extracts was determined semiquantitatively using immunochromatographic strips based on G12 antibody, in serial dilutions of the sample to represent a wide range from less than 6 ppm to over 500 ppm. Samples were diluted (1:10 to 1:20,000) in the dilution solution proposed by the manufacturer (it was tested for 6, 25, 50, 100, 250 and 500 ppm of gluten). Immunochromatographic strips were immersed in the different samples (300 µL) for 10 minutes and allowed to air dry. In this case, all individuals showed an excretion of gluten proteins/peptides in feces with values above 500 ppm (FIGS. 3A and 3B).

Once confirmed the feasibility of the method for the detection of gluten in feces, the correlation between the amount of gluten consumed and amount of gluten excreted were tested. For this, the subjects followed a controlled diet of gluten. First, these individuals consumed a strict gluten-free diet for one week, then they ingested 9 g of gluten per day divided into the main meals for a period of 4 days (taking into account the filling time of the large intestine) and finally, they consumed 30 g of gluten per day, equally divided into the main meals for a period of 4 days. In order to avoid differences in the measurement due to the ingestion of different gluten products with different origin, in all cases it was administered the same type of gluten (without heat treatment). The proposed schedule took into account that in healthy people the transit time is 45±16 hours (mean±standard deviation) with a diet rich in fiber and over 70 hours on low fiber diets (Stasse-Wolthuis et al., 1979, Am J Clin Nutr., 32:1881-1888).

Fecal samples collected during the period in which the individual followed a gluten-free diet showed, in all cases, gluten levels below the detection limit of the method (6 ppm of intact gluten, 10 ppm of hydrolyzed gluten). In contrast, when there was a 9 g intake of gluten per day it was found that the amount of gluten detected was above 250 ppm in all samples, except one which had values between 6 and 25 ppm. When individuals consumed 30 g of gluten per day the levels of gluten excreted were above 500 ppm (FIGS. 3A and 3B), more than 100 times greater than the detection limit of the method. Therefore, there is a correlation between the amount of gluten consumed and the amount of peptides with G12 epitopes excreted in feces.

In order to demonstrate the suitability of moAb G12 in the detection of gluten proteins/peptides excreted in feces, protein extracts obtained by treatment with 60% ethanol as well as controls, PWG gliadin and gluten ingested by subjects, were separated by SDS-PAGE. After that the proteins/peptides were stained with silver staining or transferred to a membrane and analyzed by Western blot with moAb G12 (FIGS. 3C and 3D). The results indicated that the moAb G12 reacts with samples derived from a conventional uncontrolled diet, GFD+9 g of gluten and GFD+30 g of gluten, as well as the positive controls, PWG gliadin and ingested gluten. However, in the sample derived from a GFD no peptides/proteins were found in feces (FIG. 3D).

EXAMPLE 3

In Vivo Monitoring of Gluten Immunotoxic Peptides in Feces from Individuals Following a Controlled Diet with Gluten This example shows how the partial digestion of reactive peptides can be determined by ELISA with the G12 anti gliadin 33 mer antibody, as convenient method, due to its simplicity, sensitivity and economy. In the case of the detection of proteins/peptides from gluten, sandwich ELISA systems are designed to quantify intact proteins but may underestimate hydrolyzed gluten. Gluten passage through the gastrointestinal tract results in the hydrolysis of the majority of it: a competitive ELISA is able to quantify toxic peptides, even at the level of a few amino acids, so it would be a convenient method for quantification.

Therefore, the aim of this study was to determine the concentration of toxic peptides present in the feces from healthy individuals by G12 competitive ELISA using as standard curve 33-mer peptide. Each experiment was carried out in triplicate on separate days. All statistical analysis was performed using SPSS software for Windows. Data were expressed as mean, maximum, minimum and percentile values 25 and 75. Differences between groups were examined using Friedman test and Wilcoxon test for comparing two related samples. A statistical probability of $p<0.05$ was considered significant.

As in the previous test, the fecal samples analyzed were the samples corresponding to the periods of intake: uncontrolled diet, GFD, GFD+9 g of gluten and GFD+30 g of gluten. Fecal samples collected during the period in which individuals followed a gluten-free diet had levels of toxic peptide below the quantification limit of the method (5.4 µg 33-mer/mg of sample). However, when they ingested 9 g of gluten per day, immunoreactive peptides were detected in feces in all cases, being in the range between 3.49 and 9.62 ng 33-mer/mg of feces, 600 times higher than the detection limit of the method. Finally, when individuals consumed 30 g of gluten per day the levels of 33-mer obtained increased in all cases, with respect to the period of ingestion of 9 g/day (6.69 to 28.00 ng 33-mer/mg of feces, $p=0.018$, with respect to GFD+9 g) (FIG. 4), more than 1,000 times higher than the detection limit of the method. These results agree with those obtained previously in the gluten detection in feces by immunochromatography. The method based on the anti-33-mer antibody could estimate the amount of gluten proteins consumed by measuring reactive peptides excreted in the feces, and the ingestion of few grams of gluten per day could be detected in quantities exceeding 600 times the detection limit. Therefore, an intake of greater than 10 mg of gluten daily could be assumed as detectable by immunological assays based on moAb G12.

EXAMPLE 4

Evaluation of Gluten Free Diet Adherence by Fecal Gluten Immunogenic Peptides Content Determination in Celiac Patients This example shows how the detection of gluten immunogenic peptides in feces samples by a sandwich ELISA test with the moAb G12 (Biomedal SL, Seville, Spain) can be used to monitor the adherence to a gluten free diet in celiac patients. The study consisted of three different groups: celiac patients (n=188) on gluten free diet for more than one year, healthy controls on a gluten containing diet (positive controls, n=84) and negative controls (babies who were only fed gluten free formula milk, n=11).

The Sandwich ELISA has an analytical sensitivity of 160 ng of gliadin 33mer peptide/g of stool. A synthetic gliadin peptide 33mer was used to make the standard curve. Either A1 or G12 moAbs reacted to different variant of the epitopes found in gliadin 33mer (Moron et al., 2008, Plos ONE, 3: e2294). Other moAbs have been described to react to epitopes found in the gliadin 33mer as R5 (r-Biopharm, Darmstadt, Germany), although the sensitivity of such recognition has not been described. The pool of peptides to which the A1 and G12 can react are defined as Gluten Immunogenic Peptides (GIP).

Subjects were instructed to collect 2-4 g of stool sample in a sealed container after recording their food intake for four days. Specimens were dropped-off within 24 hours of collection and were kept at −20° C. at all times until processing. Stool samples were incubated for 60 min at 50° C. with gentle agitation in 9 mL of Universal Gluten Extraction Solution (Biomedal SL, Seville, Spain) per gram of stool to release the gluten immunogenic peptides (GIP) from the stool matrix. After extraction, samples were diluted 1:10 and incubated for 60 min in a microtiter plate coated with G12 together with 33-mer peptide standards for quantification and the assay's positive and negative controls. Wells were then washed and samples incubated with horseradish peroxidase (HRP)-conjugated G12 antibody for another 60 min. Subsequently, plates were washed again and incubated with the HRP substrate. Color development was stopped with sulfuric acid and absorbance measured at 450 nm using a microplate reader. Each sample was run in duplicate and at least two different aliquots of each sample were tested on different days.

The moAb G12 sandwich ELISA test was able to found detectable amounts of gluten immunogenic peptides in stools of 56 (29.8%) of the 188 celiac patients examined. All 73 positive controls on a gluten containing diet except one (98.5%) had more than 160 ng of gluten peptides equivalent to the gliadin 33mer (gluten immunogenic peptides, GIP) in stools. The mean GIP concentrations obtained with this method were higher in the positive controls than in the celiac patients who had all been following a gluten free diet for more than one year. 16% of the celiac patients had a level of GIP of 160-300 ng/g stool. About 14% had more than 300 ng GIP/g stools. As expected, none of the negative controls had measurable levels of gluten immunogenic peptides (FIG. 5). These results showed that the moAb G12 sandwich ELISA assay could be a sensitive and specific method to assess gluten free diet compliance in celiac patients and that the levels of gluten immunogenic peptides in feces correlate with the amount of gluten ingested.

EXAMPLE 5

Detection of Gluten Immunogenic Peptides in Stools Correlated to Higher Frequency of Clinical Symptoms in Celiac Patients In this example, the detection of gluten immunogenic peptides in stools can be a more reliable marker of gluten free diet adherence than the serological tests traditionally used to monitor celiac patients: tissue transglutaminase antibodies and anti deamidated gliadin peptide antibodies. The levels of anti-tTG IgA and anti-DGP IgA and IgG measured in the patients' sera of the previous example 4 with the EliA™ Celikey® IgA and EliA™ Gliadin$^{DP}$ IgG kits, respectively, according to the manufacturer's protocol (Phadia, Freiburg, Germany). Anti-tTG IgA antibodies were measured in 183 (97.3%) and anti-DGP IgG in 172 (91.5%) of the 188 coeliac patients. Only samples for which both GIP and anti-tTG or anti-DGP levels were available were considered for this analysis.

There were 32 (17.5%) patients with positive anti-tTG IgA antibodies and 8 (4.4%) with indeterminate levels (FIG. 6), the remainder 143 (78.1%) were negative. Positivity for both anti-tTG IgA and GIP in stools was found in 14 (7.7%) patients (GIP strong positive=8, weak positive=6) however, anti-tTG IgA was negative in 40 (71.4%) of the 56 patients with GIP positive stools therefore there was no significant association between faecal GIP levels and IgA antibodies against tTG (p=0.230 by Fisher's exact test).

A significant association between GIP and anti-DGP IgG antibody levels (p=0.044, FIG. 7). Elevated anti-DGP IgG titres were found in 11 (6.4%) patients, 6 (3.5%) of whom were also positive for GIP in stool (4 strong positive, 2 weak positive). Indeterminate anti-DGP IgG levels were found in one (0.6%) patients and negative values in 160 (93.0%). Of these, 114 (71.3%) had undetectable levels of GIP in stools as well. Negative anti-DGP IgG antibodies, on the contrary, were present in 46 (86.8%) of the 53 GIP-stool positive patients.

Clinical data was available for 182 of the 188 participating celiac patients (FIG. 8). From them, only 9 (4.9%) reported persistent symptoms despite being on a GFD for ≥12 months (median 2.6 years range 1-5). Of these, seven were males and 2 females with a total median age of 22.4 years (range 8-46). The most frequent symptoms or analytical abnormalities were iron deficiency anemia (n=4), diarrhea (n=3), abdominal pain (n=3), weight loss (n=1), dermatitis herpetiformis (n=1), short stature (n=1) and constipation (n=1). All nine symptomatic patients had negative celiac serological markers at the time of stool sample collection except 2 (22.2%) who were positive for anti-tTG IgA and another two who were positive for anti-DGP IgA antibodies, no patients were positive for both anti-tTG and anti-DGP. Analysis of the association between presence of GIP in stools and clinical outcome revealed a significant association between GIP and symptoms typical of gluten consumption (p=0.019). Of the 9 patients with persistent symptoms, 3 (one-third) had undetectable levels of GIP in stools by GIP-ELISA, however 6 were positive indicating that gluten exposure could be responsible for the symptoms in two thirds of the celiac patients not responding to the diet. Additionally, 27.2% (47 out of 173) of the asymptomatic celiac patients had detectable levels of GIP in stools, 44.6% of them (21 cases) being strong positive. Interestingly, 5 (out of 6) of the symptomatic and 20 (out 20 of 47) of the asymptomatic GIP-stool positive patients reported gluten consumption in the food questionnaire. This could indicate inadvertent gluten consumption of those patients.

Two thirds (67%) of the celiac patients with persistent symptoms despite being on a gluten free diet had detectable levels of GIP in their stools. As both the presence of symptoms and GIP in stools may indicate potential dietary infringement, their joint use could have a higher positive predictive value for monitoring the dietary compliance of celiac patients than serological tests. About 75% of the celiac patients with detectable GIP in stools had negative serology but they had shown transgression in the diet. The detection of GIP in stools with immunomethods appeared to be more reliable than the current serological marker to monitor gluten free diet adherence.

EXAMPLE 6

Qualitative GFD Monitoring Using a Simple, Rapid Lateral Flow Test

This example shows how the object for this invention can also be applied as a qualitative rapid test to provide useful information to any person following a gluten free diet in a simple to use test format. The analytical sensitivity to achieve this should be equivalent to the one obtained with the ELISA Sandwich G12 (150 ng/g stool) if the analytical sensitivity is similar (for instance, 200-300 ng GIP/g stools). The gluten free diet is actually followed by people suffering from different conditions, not only celiac disease and the possibility of detecting gluten fragments in the stool is of interest for self-monitoring of that population following a gluten free diet. The sensitivity of the lateral flow test was about 200 ng GIP/g of stool that can be assessed by serial dilution of a solution of gluten peptide with A1/G12 epitopes, as the gliadin 33mer.

A total of 308 stool samples from newly diagnosed celiac patients on a gluten free diet for 6, 12 and more than 18 months of follow up by nutritionists were analyzed by the moAb G12 sandwich ELISA test and also by a rapid immunochromatographic test based on the A1 and G12 monoclonal antibodies (Biomedal SL, Seville, Spain). The sample collection and ELISA test procedures were the same that the ones described in example 4 and the rapid test was performed following these steps:

For gluten immunogenic peptides extraction, 0.2 g of fecal sample were mixed with 1 ml of the 50:50 alcohol-water solution provided by the manufacturer by shaking for 10 minutes. Samples were allowed to decant for 2 minutes and were diluted (1:4) in the dilution solution provided by the manufacturer. About 8 drops of the extracts were added to the A1 and G12 immunochromatographic strips covered by a plastic cassette and the results were read after 10 minutes.

The results obtained were quite similar between the rapid test and the ELISA test. The ELISA test has a higher analytical sensitivity thus obtaining higher values of positive samples detected. However, the percentage of positives is similar between the two techniques (Table 1).

TABLE 1

Detection of transgression of the gluten free diet by the G12 ELISA and the lateral flow test.

| Time on GFD | Number of samples | Positive results - ELISA Sandwich G12/G12 | Positive results - Rapid Lateral Flow Test A1/G12 |
| --- | --- | --- | --- |
| 6 months | 122 | 11% | 9% |
| 12 months | 107 | 12% | 9% |
| >18 months | 79 | 6% | 5% |

These results showed that the qualitative test at 200 ng GIP/g stools has enough sensitivity to detect a significant proportion of transgressions of the GFD. The nutritionists allowed increasing the ratio of adherence. The use of the rapid test also allowed the application of the technology for gluten peptides detection in fecal samples as a qualitative rapid test. The simplicity and sensitivity of the method make it useful as a domestic test for gluten free diet monitoring. In any case, the process can be improved by increasing the sensitivity of the immunological method.

The invention claimed is:

1. A process for monitoring gluten consumption in an individual following gluten free diet comprising:
   (a) isolating a fecal sample from said individual;
   (b) treating the fecal sample of step (a) with a hydroalcoholic solution, the treating of the fecal sample providing extracted immunotoxic gluten peptides;
   (c) contacting the extracted peptides of step b) with at least one monoclonal antibody selected from the group consisting of antibody G12, antibody A1 and antibody R5 which specifically binds the gluten immunotoxic peptides having epitopes including any sequence selected from the group consisting of SEC) ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8 and with capacity of detecting at least 6 μg gluten/g of fecal sample, the contacting of the extracted peptides with at least one monoclonal antibody forming monoclonal antibody-gluten peptide complexes;
   d) detecting the monoclonal antibody-gluten peptide complexes formed in step (c); and
   (e) quantitating the extracted immunotoxic peptides based on the detection of at least one of the monoclonal antibody-gluten peptide complexes;
   wherein the detection of at least 160 ng of extracted immunotoxic peptides per gram of feces is indicative that the individual has consumed at least 50 mg of wheat gluten per day.

2. The process for monitoring gluten consumption according to claim 1, in which step (c) is carried out by an indirect ELISA, a competitive ELISA, a sandwich ELISA, immunochromatographic strips, fluorescent immunomicroparticles, magnetic immunoparticles, Western blot, electronic biosensors or resonance biosensors.

3. The process for monitoring gluten consumption according to claim 1, in which step d) comprises detecting the complex by means of a reference standard using the peptides SEQ ID NO: 1, SEQ ID NO: 2, SEQ ID NO: 3, SEQ ID NO: 4, SEQ ID NO: 5, SEQ ID NO: 6, SEQ ID NO:7 or/and SEQ ID NO: 8.

4. The process for monitoring gluten consumption according to claim 1, further comprising providing a kit comprising:
   the hydroalcoholic solution of step b) for the extraction of gluten peptides in feces,
   a reference peptide standard comprising at least one immunogenic peptide selected from the group consisting of SEQ ID NO: 1, SEQ ID NO:2, SEQ ID NO: 3, SEQ ID NO: 4, SEQ ID NO: 5, SEQ ID NO: 6, SEQ ID NO: 7 and SEQ ID NO: 8, and
   the at least one monoclonal antibody of step c).

* * * * *

SEQUENCE LISTING

<160> NUMBER OF SEQ ID NOS: 10

<210> SEQ ID NO 1
<211> LENGTH: 33
<212> TYPE: PRT
<213> ORGANISM: Artificial Sequence
<220> FEATURE:
<223> OTHER INFORMATION: Polypeptide

<400> SEQUENCE: 1

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 2
<211> LENGTH: 6
<212> TYPE: PRT
<213> ORGANISM: Artificial Sequence
<220> FEATURE:
<223> OTHER INFORMATION: Polypeptide

```
<400> SEQUENCE: 2

Gln Pro Gln Leu Pro Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: Polypeptide

<400> SEQUENCE: 3

Gln Pro Gln Leu Pro Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Polypeptide

<400> SEQUENCE: 4

Gln Pro Gln Leu Pro Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Polypeptide

<400> SEQUENCE: 5

Gln Gln Pro Phe Pro Gln Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Polypeptide

<400> SEQUENCE: 6

Gln Leu Pro Tyr Pro Gln Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Polypeptide

<400> SEQUENCE: 7

Gln Leu Pro Phe Pro Gln Pro
1               5

<210> SEQ ID NO 8
<211> LENGTH: 7
<212> TYPE: PRT
<213> ORGANISM: Artificial Sequence
<220> FEATURE:
<223> OTHER INFORMATION: Polypeptide

<400> SEQUENCE: 8
```

```
Gln Gln Pro Tyr Pro Gln Pro
1               5

<210> SEQ ID NO 9
<211> LENGTH: 5
<212> TYPE: PRT
<213> ORGANISM: Artificial Sequence
<220> FEATURE:
<223> OTHER INFORMATION: Polypeptide

<400> SEQUENCE: 9

Gln Gln Pro Phe Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Polypeptide

<400> SEQUENCE: 10

Gln Pro Gln Pro Leu Tyr
1               5
```